United States Patent [19]

Salo et al.

[11] Patent Number: 4,587,975
[45] Date of Patent: May 13, 1986

[54] DIMENSION SENSITIVE ANGIOPLASTY CATHETER

[75] Inventors: Rodney W. Salo, Columbia Heights; Brian D. Pederson, St. Paul, both of Minn.

[73] Assignee: Cardiac Pacemakers, Inc., St. Paul, Minn.

[21] Appl. No.: 626,719

[22] Filed: Jul. 2, 1984

[51] Int. Cl.$^4$ .............................................. A61B 5/02
[52] U.S. Cl. ..................................... 128/693; 128/344
[58] Field of Search ............... 128/344, 693, 723, 734, 128/774

[56] References Cited

U.S. PATENT DOCUMENTS

| | | | |
|---|---|---|---|
| 3,347,223 | 10/1967 | Pacela | 128/734 |
| 3,837,347 | 9/1974 | Tower | 128/344 |
| 3,896,373 | 7/1975 | Zelby | 128/713 |
| 3,971,366 | 7/1976 | Motoyama | 128/734 |
| 4,182,314 | 1/1980 | Boughton | 128/693 |
| 4,299,226 | 11/1981 | Banka | 128/344 |
| 4,328,811 | 5/1982 | Fogerty | 128/774 |
| 4,332,254 | 6/1982 | Lundquist | 128/344 |
| 4,380,237 | 4/1983 | Newbower | 128/734 |

OTHER PUBLICATIONS

Vol. 18, No. 4, Jul. 1971—IEEE Transactions in Biomedical Engineering, by Gerald W. Timm and William E. Bradley; pp. 274–280.

*Primary Examiner*—William E. Kamm
*Attorney, Agent, or Firm*—Orrin M. Haugen; Thomas J. Nikolai

[57] ABSTRACT

An improved dilation catheter for use in the conduct of transluminal angioplasty techniques whereby measurements may be taken to determine patency during the course of the procedure. The catheter comprises an elongated tubular member having an inelastic expander member proximate its distal end. The expander is adapted to be inflated and deflated through the introduction of a suitable fluid into the lumen of the tubular member. Disposed on either side of the expander member are sets of electrodes, preferably ring electrodes. Associated with each such electrode is a conductor which runs the length of the catheter from an associated ring electrode to the proximal end of the catheter where such conductors are connected to circuitry for performing impedance plethysmography. Thus, as the improved catheter is routed through the vascular system, the cross-sectional size of the blood vessel at plural points proximate the distal end of the catheter can be assessed, both for locating stenotic lesions to be treated and for later determining the efficacy of the treatment process.

8 Claims, 6 Drawing Figures

DIMENSION SENSITIVE ANGIOPLASTY CATHETER

BACKGROUND OF THE INVENTION

I. Field of the Invention

This invention relates generally to surgical apparatus and more specifically to an improved catheter for use in performing transluminal angioplasty.

II. Discussion of the Prior Art

Background for understanding the surgical application of the instant invention can be obtained from the "Background of the Invention" set out in Schjeldahl et al U.S. Pat. No. 4,413,989 and the Simpson et al U.S. Pat. No. 4,323,071, which background information is incorporated herein by reference.

It is deemed helpful to the successful use of transluminal angioplasty procedures if means are provided for precisely locating the site of the stenotic lesion to be treated so that the expander member on the catheter can be positioned adjacent that site such that, when the expander member is inflated, the stenotic lesion will be compressed into the endothelial tissue of the blood vessel being treated. In the past, it has been the practice to use X-ray or fluoroscopic observation where a suitable radiopaque dye is introduced to render the obstruction visible. The present invention also provides the possibility of determining the composition of the plaque (the degree of calcification) by the frequency dependence of the impedance. Hence, by suitable selection of the driving frequency, the characteristics of the lesion can be determined.

SUMMARY OF THE INVENTION AND OBJECTS

The present invention is directed to a dilating catheter assembly which incorporates a means whereby the cross-sectional size of a blood vessel may be measured while routing the catheter through the vascular system to the site of the stenotic lesion to be treated. By measuring the vessel's cross-section on either the proximal or distal side of the expander on a continuous basis, it is possible to precisely position the expander relative to a constriction to be treated. For example, when performing a percutaneous transluminal coronary angioplasty, as the catheter is advanced through the vascular system with the distal end entering a coronary artery, if a first measurement taken distally of the expander shows a decrease in vessel cross-section followed by an increase while that sensed proximally of the expander remains at the larger size, it is known that the expander is juxtaposed at the location of the stenotic lesion. Now, a suitable fluid may be introduced through the proximal end of the catheter to inflate the expander member to a predetermined maximum size and pressure and thereby press the lesion into the wall of the coronary artery. Following this step, the catheter can be retracted slightly and the cross-sectional area measurements can be repeated to determine the improved patency of the coronary artery.

The catheter itself comprises an elongated tubular member having an inexpandable, extensible expander (balloon) disposed near it distal end. As is described in the aforereferenced Simpson et al patent, the wall of the tubular member may be provided with ports disposed between the spaced-apart ends of the expander member, which ends are sealingly joined to the exterior of the tubular member. Thus, by injecting a suitable fluid into the lumen of the tubular member at its proximal end, the expander can be inflated. Disposed distally at the distal end of the expander member are a plurality of electrodes which are spaced longitudinally from one another. A similar plurality of electrodes are preferably disposed proximally of the proximal end of the expander member, again in a predetermined spaced relationship. In practice, it has been found convenient to affix ring or spot electrodes on the surface of the catheter, these electrodes being spaced from one another along the longitudinal axis of the catheter and on either side of the expander. The individual electrodes are connected by suitable conductors which run the length of the catheter, either through a lumen of the tubular member or within its walls so that the ends of the conductors assessible at the proximal end of the catheter.

The electrical conductors connected to the surface electrode are adapted to be coupled through conventional means to suitable switching circuitry such that selected electrode pairs may have an alternating current signal impressed across them. Other electrode pairs may then be used to make impedance measurements, which impedance measurements are proportional to the cross-sectional area of the portion of the vessel disposed between the two impedance sensing electrodes. By utilizing the angioplasty catheter of the present invention, the surgeon is provided with instantaneous indications of the relative size of the lumen of the blood vessel being treated at the site of the balloon or expander.

It is accordingly a principal object of the present invention to provide a new and improved catheter assembly for performing percutaneous transluminal angioplasty.

Another object of the invention is to provide a dilating catheter for performing percutaneous transluminal angioplasty in which the catheter includes electrode means for accommodating impedance plethysmography.

Yet another object of the invention is to provide a dilating catheter assembly which can be readily inserted through the vascular system while measurements are taken of the cross-sectional size of the blood vessel being traversed by the catheter.

Still another object of the invention is to provide a dilating catheter assembly of the above character in which a distensible expander member is disposed on the catheter near its distal end and where plural electrode surfaces are exposed on the surface of the catheter assembly on both sides of the expander member.

Additional objects and features of the invention will appear from the following description in which the preferred embodiment is set forth in detail in conjunction with the accompanying drawings in which like numerals in the several views refer to corresponding parts.

DESCRIPTION OF THE PREFERRED EMBODIMENT

Figure 1:
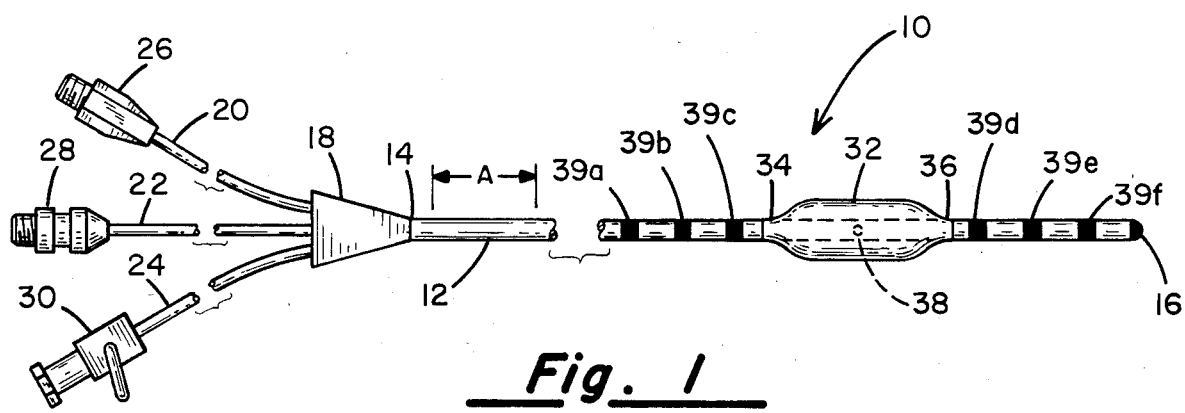
FIG. 1 is a side elevation view of the dilating catheter in accordance with the present invention.

Referring first to FIG. 1, there is indicated generally by numeral 10 an improved catheter in accordance with the preferred embodiment of the invention. While the catheter 10 will be shown and described as a catheter intended to be used during coronary transluminal angioplasty (CTA), it is to be understood that a catheter, following the teachings of the present invention, can be used in examining and treating body organs other than the heart and, accordingly, the invention is not to be limited to the CTA application only. The CTA catheter assembly 10 includes an elongated, flexible, plastic outer tubular member 12 which, for reasons which would become apparent from the following description, is referred to as the expander mounting tube. The member 12 has a proximal end 14 and a distal end 16.

The proximal end 14 of the catheter assembly 10 joins to a coupler 18 of conventional design, the coupler allowing other tubular members 20, 22 and 24 to communicate with one or more of the lumen contained within the outer tubular member 12. Depending upon the particular application, suitable adapters as at 26, 28 and 30 may be employed to connect the CTA catheter to appropriate fluid sources and/or instrumentation.

The expander mounting tube 12 may typically be a six French catheter but limitation to such a size is not to be inferred. Also, it may be found expedient to taper the distal end of the expander mounting tube 12 to facilitate its entry through an ostium and into a coronary artery.

Surrounding the distal end portion of the expander mounting tube 12 is an expander 32 which, in FIG. 1, is shown in its extended or inflated condition. The expander 32 is preferably formed from a suitable synthetic plastic material, such as biaxially-oriented polypropylene with the expander being formed in an injection blow molding operation such that it is substantially inelastic in both the axial and radial directions. The expander member 32 is suitably bonded to the outer surface of the expander mounting tube 12 as at 34 and 36 so that the port 38 formed through the side wall of the expander mounting tube 12 and communicating with its lumen is spanned by the expander member 32. The introduction of a suitable fluid through the lumen of the expander mounting tube 12 may flow through the port 38 so as to inflate the expander member or balloon 32 to its maximum designed diameter.

Formed proximally of the expander member 32 are a series of spaced, conductive, surface electrodes 39a, 39b, 39c, etc. Similarly, positioned on the surface of the expander mounting tube 12 distally of the expander member 32 are a further plurality of surface electrodes 39d, 39e, and 39f. While the electrodes 39 are indicated as being surface ring electrodes, it is not a requirement that such electrodes be a continuous band completely surrounding the expander mounting tube.

Having described the external characteristics of the preferred embodiment, consideration will next be given to its internal construction and, in this regard, the cross-sectional view of FIG. 2 will be referred to. In this view, the distal end portion of the catheter assembly 10 is illustrated in a greatly enlarged scale as being located within the lumen of an artery 40, and along the inner walls of this artery is a buildup of plaque as at 42. The expander member 32 is shown in its inflated condition whereby the stenotic lesion or plaque 42 is in the process of being compressed into the endothelial layer of the artery 40 as during a typical angioplasty procedure.

Figure 2:
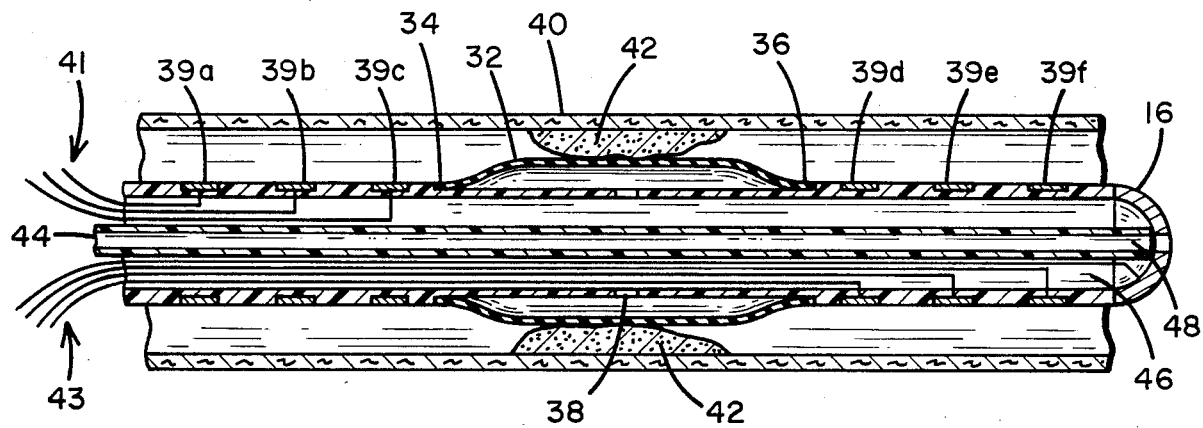
FIG. 2 is a greatly enlarged cross-sectional view of the distal portion of the catheter of the present invention when positioned in an artery during percutaneous transluminal angioplasty.

Also revealed in the cross-sectional view of the FIG. 2 is a coaxially-arranged pressure sensing tube 44, which is located within the lumen 46 of the expander mounting tube 12 and which extends the full length of the catheter from the connector assembly or coupler 18 to the distal tip 16. The outside diameter of the pressure sensing tube 44 is less than the inside diameter of the expander mounting tube 12 and, as such, a clearance is provided through which the fluid for expanding the expander member 32 may flow. The inner lumen 48 of the pressure sensing tube 44 may be coupled by means of the connector 26 to a suitable manometer whereby blood pressure distally of the expander member can be monitored. This same lumen may also be used, when desired, to inject medicaments and/or radiopaque dye and the like for rendering the stenotic lesions visible on the screen of a fluoroscope.

The ring electrodes 39a, 39b and 39c are connected by electrical conductors 41 to connector pins of a suitable plug 28 and, similarly, the ring electrodes 39d, 39e and 39f are connected by electrical conductors 43 to other pins in the electrical plug 28. In the view of FIG. 2, the electrical leads or wires 41 and 43 are routed through the lumen 46 of the expander mounting tube 12 from their associated electrodes to the adaptor plug 28.

Figure 4:
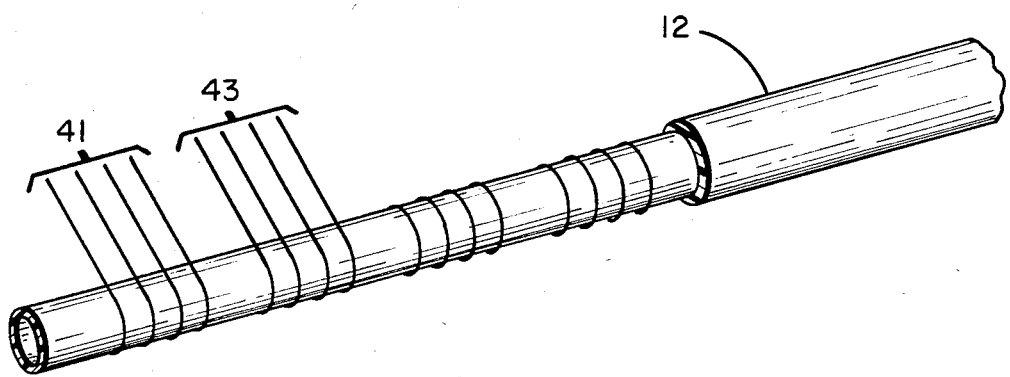
FIG. 4 is a partial cross-sectional view illustrating an alternative way of routing electrical conductors to the electrode segments on the catheter.

FIG. 4 illustrates an alternative way of routing the electrical wires from the electrical connector 28 through the lead 22 and the coupler 18 to the individual electrodes at the distal end of the catheter assembly 10. Here, rather than being routed longitudinally through the lumen 46, the wires 41 leading to the proximal electrodes and the wires 43 leading to the distal electrodes may be helically wound and embedded within the walls of the expander mounting tube 12. The manner in which such a catheter may be constructed is fully set out in co-pending application Ser. No. 445,240, filed Nov. 29, 1982, for "CATHETER ASSEMBLY", which is assigned to the assignee of the instant application.

Figure 3:
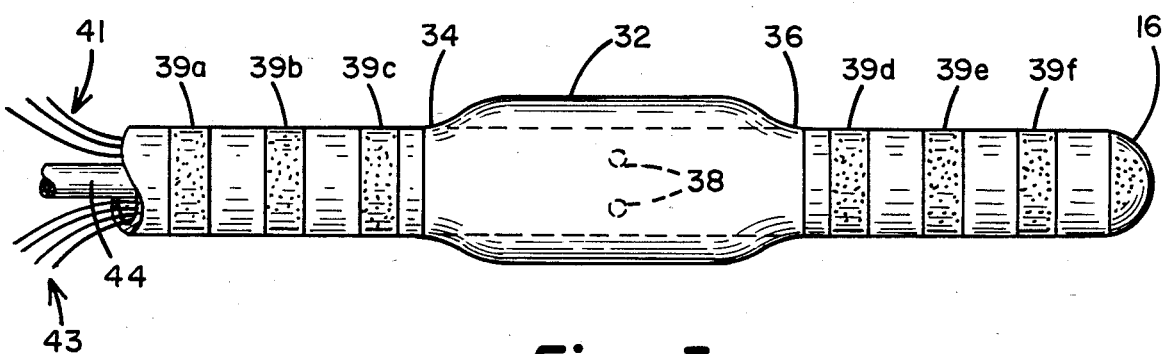
FIG. 3 is a greatly enlarged distal end segment of the dilating catheter of FIG. 1.

Irrespective of the method employed, electrical connections are individually brought out at the proximal end of the catheter from each of the surface electrodes 39a through 39f. While in FIGS. 2 and 3, only three such electrodes are shown distally and proximally of the expander member 32, it will be apparent to those skilled in the art that a greater or fewer number of such surface electrodes may be provided. Furthermore, the manner in which surface electrodes may be formed on the exterior surface of the expander mounting tube 12 may be the same as is used in forming a ring electrode on a bipolar-type pacing lead conventionally used with heart pacemakers.

Referring again to FIG. 1, the coupler 30 comprises a fluid valve member which is in fluid communication via the tube 24 to the lumen of the catheter which communicates via ports 38 with the interior of the expander member 32. It is by way of the valve member that the connector 28 is an electrical plug which is adapted to mate with the circuitry yet to be described for the purpose of conducting impedance plethysmography. The coupler or connector 26 may be joined or pressure-sensing equipment and/or selectively to a source of radiopaque dye or other medicaments, the tube 20 joining in the coupler 18 with the pressure sensing tube 44 of the catheter assembly.

Figure 5:
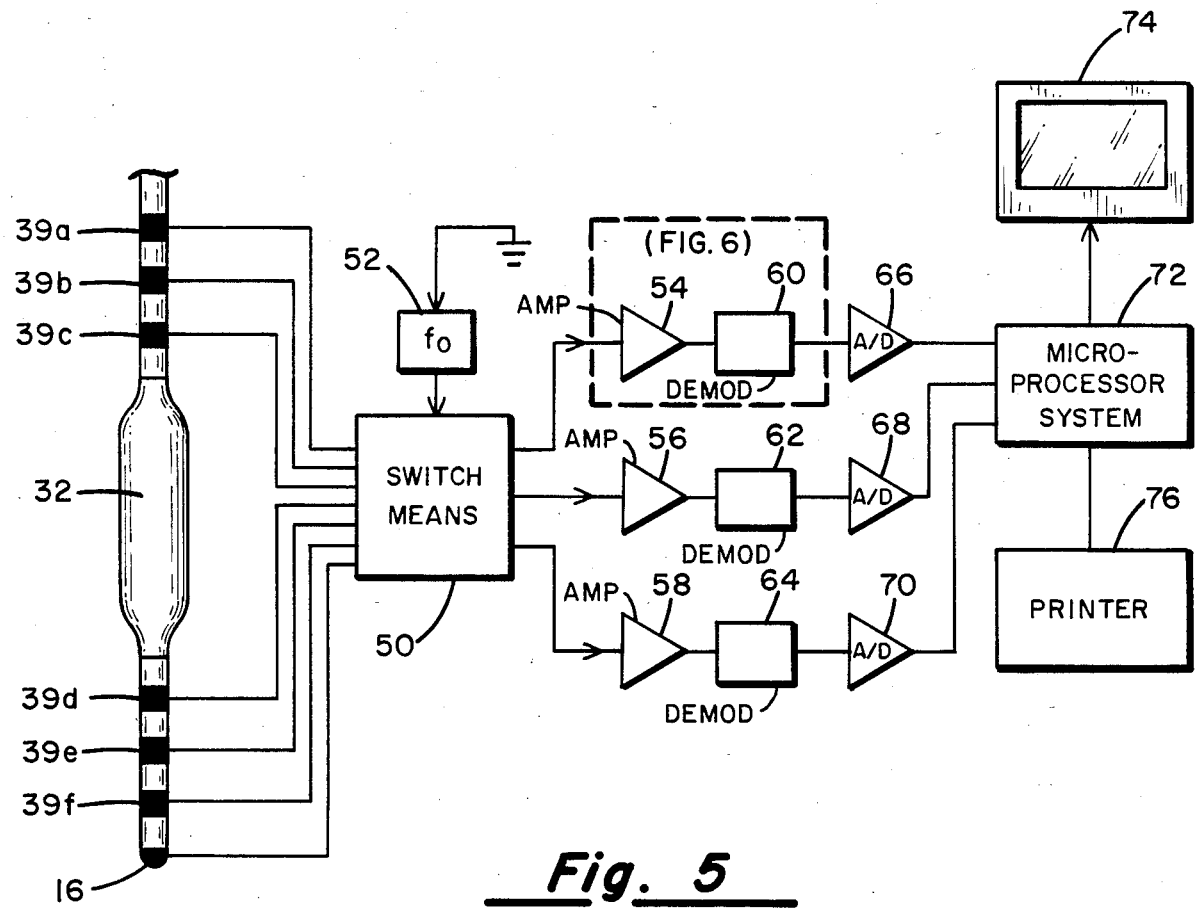
FIG. 5 is an electrical block diagram for obtaining and displaying information concerning the cross-sectional size of a blood vessel in which the catheter of the present invention is located.

Referring next to FIG. 5, each of the surface electrodes 39a through 39d is coupled via the connector 28 to a switch means 50. Also coupled as an input to the switch means is a suitable oscillator 52 for applying a voltage of a frequency $f_0$ across two preselected surface electrodes 39a through 39d, all as determined by the setting of the switch means 50. The particular pair of surface electrodes which are coupled through the switch means 50 to the oscillator 52 may be referred to as the driving electrodes. The remaining electrodes which are disposed between the pair of driving electrodes function as sensing electrodes and are effective to pick up electric field signals existing at the site of the sensing electrodes occasioned by the introduction of a current flow in the fluid (blood) between the spaced-apart driving electrodes.

As will be set out in greater detail below, the impedance presented to the current is dependent upon the conductivity of the fluid (blood) or tissue in the local area defined by a cooperating pair of sensing electrodes and this conductivity is, in turn, dependent upon the cross-sectional area of the blood vessel at the site of the sensing electrodes and the presence of any sclerotic tissue. The electrical signals picked up by the sensing electrodes pass through the switch means 50 to the input of a set of isolation amplifiers 54, 56 and 58. From there, the signals are fed through demodulator networsk 60, 62 and 64. The implementation of the oscillator/driver 52 isolation amplifiers 54 and the demodulator 60 is shown in FIG. 6 and these circuits will be described in greater detail hereinbelow.

The output from the demodulators 60–64 are, in turn, fed to a set of analog-to-digital converters 66, 68, and 70 which function to create a digital number proportional to the analog signal developed at the output of the demodulators 60–64. Once so digitized, these values may be applied as inputs to a suitable microprocessor system 72 where, in accordance with a program of instructions, can be suitably processed for presentation either on a video monitor 74 or on a hardcopy printer 76.

Figure 6:
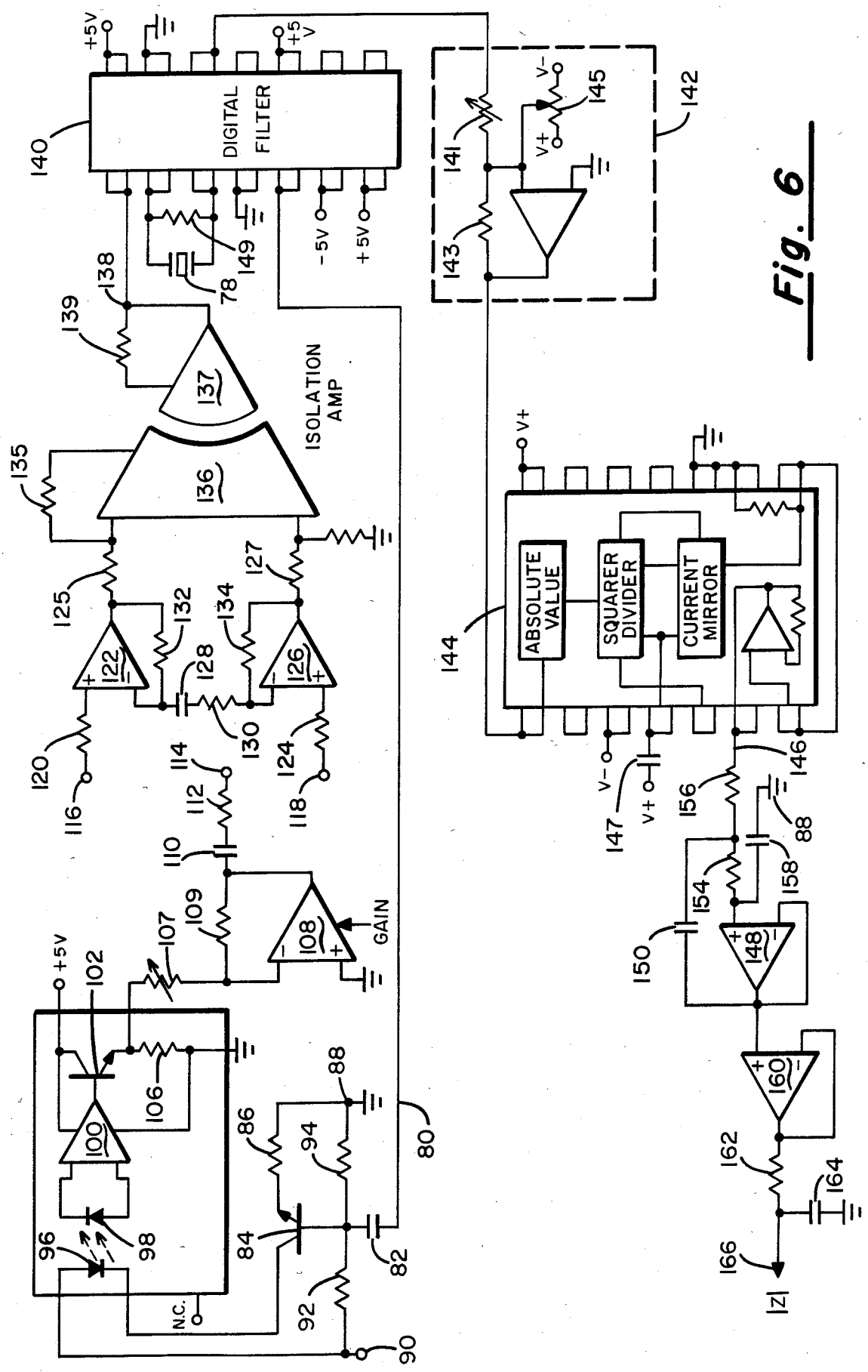
FIG. 6 is an electrical schematic diagram of the isolation amplifiers and the modulators needed to extract the sensed electrical signal proportional to cross-sectional size of a portion of the blood vessel in which the catheter of the present invention is inserted.

Referring now to FIG. 6, the carrier frequency for driving the outer electrodes 39a and 39f includes a Type 3576 digital band-pass filter having a crystal 78 connected across appropriate terminals thereof. It incorporates a tone-generator, a band reject filter, a band-pass filter and an output driver. A digitized sine wave signal is generated at the output pin 5 of the device, the sine wave having a frequency equal to that of the center frequency of the digital filter, e.g. 2,600 Hz. This signal is applied via conductor 80 and through a coupling capacitor 82 to the base electrode b of a transistor 84. This transistor has its emitter electrode e connected through a current-limiting resistor 86 to ground point 88. A source of potential is adapted to be connected to the terminal 90, which is coupled via a resistive voltage divider, including resistors 92 and 94, to the ground point 88. The base electrode b of the transistor 84 is connected to the common terminal of the resistive voltage divider and, by properly selecting the ohmic values of these two resistors, the transistor may be biased for Class-A operation. When so configured, a sine wave current corresponding in frequency to the signal on line 80 is made to flow from the positive voltage source terminal 90, through a light-emitting diode 96 and through the emitter-to-collector path of the transistor 84 and the current-limiting resistor 86 to ground. Thus, the light energy given off is sinusoidal in nature and is adapted to a photo-detector device 98 connected across the input terminals of an operational amplifier 100 which is configured to function as a linear amplifier. Specifically, the output from the linear amplifier 100 is connected to the input or base electrode of a NPN transistor stage 102. The output from this stage is developed across the resistor 106 connected in its emitter circuit and is applied to the inverting input of an adjustable gain amplifier 108. Because of the manner in which the opto-coupler is configured, the voltage appearing at the emitter electrode of the transistor 102 is a voltage which is proportional to the current flowing through the LED device 96. The amplified signal emanating from the amplifier device 108 is applied through a coupling capacitor 110 and a resistor 112 to the particular ring electrode selected by the switch means 50 of FIG. 5. The voltage appearing at the terminal point 114 is taken with reference to the tip electrode of the catheter.

With continued reference to FIG. 6, the terminals 116 and 118 are arranged to be coupled to the conductors associated with the particular driven ring electrodes selected by the switch means 50 of FIG. 5. Terminal 116 to which one of the sensing electrodes is selectively connected is coupled through a resistor 120 to the non-inverting input of an operational amplifier 122. Similarly, the terminal 118 which is selectively coupled to another sensing ring electrode is connected through a coupling resistor 124 to the non-inverting input of an operational amplifier 126. The operational amplifiers 122 and 126 have their feedback components connected so as to cause them to function as high-pass filter means. Specifically, a series connection of a capacitor 128 and a resistor 130 is connected between the inverting input of the operational amplifier 122 and the inverting input of the operational amplifier 126. Feedback resistors 132 and 134 are respectively coupled from the output of the operational amplifiers 122 and 126 back to the outer terminals of the serially connected components 128 and 130. The component values are selected such that the high-pass filter has a cut-off frequency of approximately 50 Hz, which allows the modulated carrier signal to pass through the filter stage while rejecting the lower frequency artifacts which may be occasioned by electrocardiographic signals and muscle noise.

The output from the high-pass filter is applied across the inputs of a Type 3656 instrumentation amplifier which has a high input impedance and a transformer coupled isolation amplifier incorporated therein. This device provides multi-port isolation of both power and signal and, as such, is readily suited to biomedical applications because of the resulting elimination of shock hazards. The output from the amplifier appearing at terminal point 138 is directly coupled to input pin 1 of the digital filter network 140. The digital filter network 140 comprises an extremely high-Q band-pass filter, which is turned or set to pass the modulated carrier signal while rejecting artifacts such as P-waves, T-waves, R-waves, etc.

The output from the digital filter 140 is applied via an offset gain stage 142 to the input of a so-called "True RMS Converter". The offset gain stage 142 is included to merely provide calibration factors for permitting limited adjustment of signal amplitudes and the like.

The True RMS Converter 144 functions to directly compute the true root mean square value of any complex waveform containing ac and dc components and yields an equivalent dc output level. Thus, it will act as a demodulator circuit for separating the alternating current carrier signal from the wave which is modulating it. Thus, a signal proportional to the modulation envelope of the carrier appears on the conductor 146 and is applied to a low-pass filter stage comprising an operational amplifier 148 having a feedback capacitor 150 connected between the output from the amplifier and a junction point 152 formed at the common connection between series connected resistors 154 and 156. To provide the low-pass characteristics, a further capacitor 158 is coupled between the non-inverting input of the operational amplifier 148 and ground point 88.

The low-pass filter network is configured to have a center frequency $f_c$ equal to approximately 50 Hz and is effective to remove ripple from the output signal. The resulting low frequency signal passing through the filter stage is applied to a further operational amplifier which is configured to function as a buffer or isolation circuit 160.

Providing further low-pass filtering to the signal emanating from the buffer stage 160 are a series resistor 162 and a shunt capacitor 164. The signal appearing at terminal 166 is thus directly proportional in amplitude to the impedance being monitored which, as indicated, is directly proportional to the size of the blood vessel in which the selected sensing electrodes find themselves.

Those skilled in the art will recognize that for each pair of sensing electrodes there will be one such isolation amplifier and demodulator configuration, i.e., the combination of circuitry shown between the input terminals 116 and 118 and the output terminal 166.

In implementing the isolation amplifier/demodulator system of FIG. 6, it has been found that component types and component values as set forth in the following table have produced an operable embodiment. However, it is to be understood that the invention is not to be limited to this particular circuit arrangement or to the component types and values indicated.

| Component | Value/Type |
| --- | --- |
| R 86 | 510 ohms |
| R 92 | 12 K ohms |
| R 94 | 6.8 K ohms |
| R 106 | 2 K ohms |
| R 107, 141 | 100 K ohms variable |
| R 109, 124, 127, 139, 143 | 100 K ohms |
| R 112 | 200 K ohms |
| R 120, 124 | 10 K ohms |
| R 132, 134, 135, 154, 156 | 1 megohm |
| R 145 | 20 K variable |
| R 149 | 10 megohms |
| R 162 | 470 ohms |
| C 82, 110 | 1.0 microfarads |
| C 128, 147 | 0.1 microfarads |
| C 158 | 0.001 microfarads |
| C 164 | 2.2 microfarads |
| Opto-coupler | MOC 5010 |
| Op Amps (all) | TL 064 |
| Instrumentation Amp | Burr-Brown 3656 |
| Digital Filter | S-3526 (Advanced Microsystems, Inc.) |

-continued

| Component | Value/Type |
| --- | --- |
| True RMS Converter | AD 536 (Analog Devices, Inc.) |

OPERATION

In carrying out an angioplasty procedure, the catheter of the present invention is introduced using the Seldinger technique, usually into the femoral artery and is routed through the vascular system, through a coronary ostium and into a selected one of the coronary arteries. Once so located, the circuit of FIG. 6 can be energized and the selector means 50 of FIG. 5 is used to cause an alternating current carrier signal from the digital filter network 140 to be applied to the base of Class A amplifier transistor 84. Thus, the light energy emitted by the LED 96 is similarly controlled in sinusoidal fashion, producing a carrier voltage on the emitter electrode of the opto-coupler transistor element 102 which is proportional to the current flowing through the LED. This signal is, in turn, then adjusted by the network 108 including the variable resistor 107 and the fixed resistor 109, with the resulting sinusoidal signal being applied between the switch-selected driven ring electrode and the isolated ground point associated with the tip electrode.

As was explained earlier in the specification, the impedance presented to the current flowing between the driven electrodes varies in relation to the inflow and outflow of blood in the coronary artery and also to its cross-sectional dimensions. This causes the sinusoidal carrier signal to be modulated and the resulting modulated carrier is developed between selected pairs of sensing electrodes which are coupled, via the elongated conductors flowing through the length of the catheter body connected to the terminal points 116 and 118 of the instrumentation amplifier. Specifically, the capacitor 128 and resistor 130 when connected as indicated in FIG. 6 to the operational amplifiers 122 and 126, function as a high-pass filter. The output of the high-pass filter is applied to the Burr-Brown Type 3656 transformer coupled isolation amplifier halves 136 and 137.

The initial high-pass filter stage at the input of this isolation amplifier serves to remove the ECG and DC offset components of the input wave form which may be superimposed on the modulated carrier by tissue depolarization and "electrode effects".

The output from the transformer coupled isolation amplifier stage 137 is, in turn, connected as an input to the digital filter network 140. This filter network is arranged to function as a high-Q band pass filter having a very narrow pass band centered about the frequency developed by the crystal element 78. By setting this frequency at about 2,600 Hz, one is sure to strip off from the modulated carrier signal any remaining artifacts due to ECG or electrical noise. The output from the digital filter network is then increased by properly setting the potentiometer 145 and the variable resistor 141 so that calibration can take place.

To provide the necessary demodulation of the modulated carrier, the composite wave form is applied to a Type AD 536 True RMS Converter. This is an integrated circuit chip which functions to convert the rms value of the applied signal to a dc level. The resulting output signal developed on conductor 146 effectively comprises the modulating envelope, and it is applied as an input signal to a low-pass filter whose cutoff is set at about 15 Hz. The filter includes the operational amplifier 148 and its associated feedback capacitor 150 an input shunt capacitor 158. The resulting dc signal is proportional to the cross-sectional size of the blood vessel in which the selected pair of sensing electrodes are then positioned. The signal may further be buffered by an operational amplifier 160 to provide appropriate matching to down-stream components such as analog-to-digital converting circuitry (see FIG. 5).

By monitoring changes in the value of the magnitude of the impedance 1Z1, a cardiovascular surgeon is in a better position to know the characteristics of the interior of the artery being treated. Furthermore, he is better able to locate plaque buildup on the interior walls of the coronary arteries or other blood vessels being investigated. This aids in properly positioning the expander member relative to the potential obstruction. Then, appropriate fluids are introduced through the lumen of the catheter so as to expand the expander member at the tip thereof, pressing the stenotic lesion back into the wall of the blood vessel where it tends to be reabsorbed.

Through proper use of the switching means 50, the physician is able to monitor dimensional characteristics, both proximally and distally of the expander member. As already mentioned, this is a great aid in the proper positioning of the angioplasty catheter.

The invention has been described in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

What is claimed is:

1. Angioplasty catheter having means for indicating blood vessel wall dimensions comprising, in combination:
    (a) an elongated tubular body having a longitudinally extending lumen and a proximal end and a distal end with an expander member affixed near said distal end, said expander member being in fluid communication with said lumen of said tubular body;
    (b) a plurality of electrodes disposed on the surface of said tubular body proximate said expander member;
    (c) signal generator means connected to the proximal end of said catheter body for applying an alternating current carrier signal between first and second of said plurality of electrodes, said carrier signal being modulated by the changes in blood flow through said blood vessel; and
    (d) signal processing means connected to third and fourth of said plurality of electrodes for developing a direct current signal proportional to the cross-sectional size of a blood vessel in which said distal end of said catheter body is disposed.

2. The angioplasty catheter as in claim 1 wherein said third and fourth electrodes are disposed between said first and second electrodes.

3. The angioplasty catheter as in claim 2 wherein said first electrode is disposed distally of said expander member and said second electrode is disposed proximally of said expander member.

4. The angioplasty catheter of claim 2 and further including switching means connected between said signal generator means and said plurality of electrodes for selecting at least one pair of said plurality of electrodes for energization by said signal generator means.

5. The angioplasty catheter of claim 4 wherein said switching means further includes means for coupling selected electrode pairs to said signal processing means.

6. The angioplasty catheter as in claim 1 wherein said signal generator means comprises:
    (a) oscillator means for developing an alternating current voltage;
    (b) an opto-coupler having a radiant energy emitting means driven by said alternating current voltage, and photo-diode means positioned to receive said radiant energy; and
    (c) amplifier means connected to said photo-diode means for producing an output voltage proportional to the current flowing through said radiant energy emitting means, said output voltage of said amplifier means being coupled to said first and second electrodes.

7. The angioplasty catheter as in claim 6 wherein said demodulator means includes:
    (a) band-pass filter means coupled to receive the output from said isolation amplifier means; and
    (b) rms to dc converting means responsive to the output from said band-pass filter means for producing a dc signal related to said modulating signal, said dc signal varying in accordance with changes in the cross-sectional size of the blood vessel in which said first and second electrodes are positioned during use.

8. The angioplasty catheter as in claim 1 wherein said signal processing means comprises:
    (a) isolation amplifier means coupled to said third and fourth electrodes for receiving and amplifying a modulated version of said alternating current carrier signal;
    (b) demodulator means for recovering the modulating signal from said modulated version of said carrier signal;
    (c) analog-to-digital converter means for converting said modulating signal to a digital representation thereof; and
    (d) display means for presenting data relating to the positioning of said angioplasty catheter in the vascular system of a patient.

* * * * *